United States Patent [19]  [11] 3,984,535
Ghilardi et al.  [45] Oct. 5, 1976

[54] SCALP DEODORANT COMPOSITION

[75] Inventors: Giulana Ghilardi; Régine Pasero, nee Perruche, both of Paris, France

[73] Assignee: L'Oreal, Paris, France

[22] Filed: June 9, 1975

[21] Appl. No.: 584,723

Related U.S. Application Data

[63] Continuation of Ser. No. 426,824, Dec. 20, 1973, abandoned, which is a continuation of Ser. No. 164,952, July 21, 1971, abandoned.

[30] Foreign Application Priority Data

July 24, 1970 Luxemburg ............................ 61405

[52] U.S. Cl. .................................... 424/47; 424/65; 424/70; 424/308; 424/319; 424/346
[51] Int. Cl.² ................ A61K 7/32; A61K 31/235; A61K 31/195; A61K 31/05; A61K 7/06
[58] Field of Search ................... 424/47, 65, 70, 76, 424/308

[56] References Cited
UNITED STATES PATENTS 2,226,177  12/1940  Orelop et al. ........................... 424/65
3,462,534  8/1969  Greengard et al. .................. 424/308
3,729,563  4/1973  Cash et al. ........................... 424/308

FOREIGN PATENTS OR APPLICATIONS 1,351,454  2/1964  France

OTHER PUBLICATIONS

American Perfumer & Cosmetics, 1st Documentary Ed. 1960, pp. 114, 119, 120-134, 218 and 281.

*Primary Examiner*—Donald B. Moyer
*Attorney, Agent, or Firm*—Cushman, Darby & Cushman

[57] ABSTRACT

A scalp deodorant composition contains as the active ingredient 2,6-di.tert. butyl paracresol, propyl gallate, butyl hydroxy anisol, octyl gallate or dodecyl gallate. The dermatologically acceptable carrier for the active ingredient can be water or a lower alkanol or a mixture thereof. The active ingredient is present in amounts of about 0.1–3 weight percent of the composition.

8 Claims, No Drawings

SCALP DEODORANT COMPOSITION

This is a continuation of application Ser. No. 426,824, filed Dec. 20, 1973, which in turn is a Rule 60 continuation of Ser. No. 164,952, filed July 21, 1971 both now abandoned.

This invention relates to a novel cosmetic composition and more particularly to a novel deodorant composition for application to the scalp.

It has been found that certain heads of hair or certain scalps release an odor which generally is not pleasant. This odor will be called hereafter "hair odor" and it is believed to be associated or produced by secretions from the scalp which on contact with surface bacteria of the skin can act on the lipid content of the secretions to form odorous compounds.

It has been observed that this odor, which can temporarily be eliminated by shampooing, quickly recurs and even in the absence of outside dirt.

Studies made by the applicants to combat or eliminate this "hair odor," revealed that the use of conventional body deodorants was ineffective, whereas certain phenolic derivatives effectively combatted this odor.

It has also been found that at the time of application of these compounds in suitable dermatologically acceptable carriers, they exhibit not only an effective deodorizing action but they appear to retard the secretion of sebum from the scalp and thus advantageously improve the condition of the scalp as well as the cosmetic appearance of the hair which is less greasy, softer and does not stick or mat.

The application of the compositions of this invention containing the novel phenolic derivatives as the active ingredient appear to effect a significant reduction of sebum secretion from the scalp, due, it is thought, by a partial blockage of the external openings or a modification of the glands, in the sense that there is a reduction of flow of sebum therefrom.

To confirm the deodorizing action and reduction of sebum secretion characteristics of the phenolic derivatives of the present invention, deordorant compositions containing the same were applied to the hair of persons whose scalp presented either a marked odor or an excessive secretion of sebum, or both at the same time.

Comparative tests were made by parting the hair in the middle, half of the head being subjected to a treatment with a composition according to the invention, the other half of the head being treated, either:

a. with a similar composition but not containing the phenol derivative(placebo), or b. with a composition containing S-carboxy methylcysteine which has been found to effectively reduce excessive secretion of sebum from the scalp.

Two series of tests were made. In a first series, compositions according to the present invention are applied weekly in the form of a lotion after a shampoo containing a simple cleansing agent. After application of the lotion and without rinsing, the hair is set.

Another series of tests comprise, besides weekly lotions, a daily application of the compositions of this invention in the form of a spray having a slight content of nonvolatile product.

These tests made it possible to establish the deodorizing action and excessive sebum secretion reducing characteristics of the compositions according to the present invention.

It is therefore a principal object of the present invention to provide scalp deodorant composition comprising in solution a phenolic derivative.

Another object of the present invention is the provision of a scalp deodorant which also effectively reduces excessive secretion of sebum from the scalp and thereby effectively inhibits or retards the recurrence of scalp odors.

In accordance with the present invention, the novel scalp deodorant comprises a solution in a solvent selected from the group consisting of water, lower alkanols and mixtures thereof of a phenolic derivative selected from the group consisting of butyl hydroxy toluene, butyl hydroxy anisol, propyl gallate, octyl gallate and dodecyl gallate. Preferably, the lower alkanol is ethyl or isopropyl alcohol, present in amounts ranging from about 90 to 96 percent by weight to said composition. When aqueous alcohol solutions are employed, the solution contains about 10 to 50 percent by weight of said lower alkanol.

Of said compounds, 2,6-di tert. butyl paracresol, the preferred butyl hydroxy toluene, having the formula:

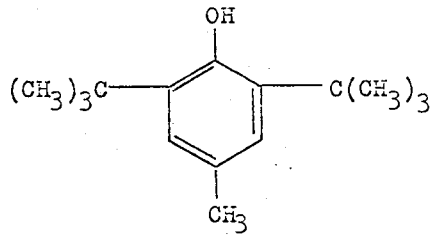

and propyl gallate having the formula

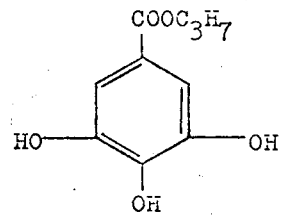

are preferred since these compounds are essentially free from any markedly characteristic odor, are non-irritating to the scalp, do not materially interfere with the combing or setting of the hair and do not dull the hair or cause it to stick or mat.

While useable in the present invention, although less preferred, butyl hydroxy anisol has a peculiar odor, octyl gallate can cause some nasal irritation and dodecyl gallate can occasion some scalp irritation.

To be effective, the capillary compositions should contain at least 0.1% of the active compounds according to the invention. The maximum amount of the active compound incorporated in the composition is limited by the amount of deposits on the hair. These deposits should not make the hair sticky or clinging.

It is preferred to incorporate in the capillary compositions an amount of said active compound not exceeding 3%, this amount preferably being between 0.5 and 1%.

The capillary compositions containing the active compound in solution can be in the form of a lotion, mist, spray, or packaged under pressure in an aerosol container with a conventional aerosol propellant such as dichlorodifluoromethane, trichloromonofluoromethane or mixtures thereof. Generally, the propellant comprises about 90 to 50 weight percent of the total sprayable composition. The pH of the compositions of this invention generally ranges between 2–10 and preferably between 3–7.5.

When in lotion form, the compositions are generally applied after shampooing, while when in an aerosol spray form they can be applied daily, in which case they have a slight content of "dry spray" non-volatile materials such as a film forming polymer having a molecular weight ranging from about 10,000–150,000, so as not to harm the holding of the setting. Representative film forming polymers include polyvinyl pyrrolidone and polyvinyl pyrrolidone/vinyl acetate copolymers having a monomer ratio range of 70:30 to 30:70.

The following examples illustrate the present invention:

EXAMPLE 1

The following scalp deodorant composition is prepared:

| | |
|---|---|
| propyl gallate | 1 g |
| ethyl alcohol | 30 ml |
| perfume | 0.1 g |
| water sufficient for | 100 ml |

The pH of this lotion is 5.5.

EXAMPLE 2

A scalp deodorant composition, in lotion form is prepared as follows:

| | |
|---|---|
| propyl gallate | 1 g |
| ethyl alcohol | 45 ml |
| perfume | 0.1 g |
| water sufficient for | 100 ml |

The pH of this lotion is 5.5.

EXAMPLE 3

Another scalp deodorant composition, in accordance with the present invention is prepared as follows:

| | |
|---|---|
| propyl gallate | 1 g |
| polyvinyl pyrrolidone/vinyl acetate copolymer, a film-forming agent sold by the General Aniline Company under the name of "PVP/VA S.630" | 1 g |
| ethyl alcohol | 45 ml |
| perfume | 0.1 g |
| water sufficient for | 100 ml |

The pH of this lotion is 5.4.

EXAMPLE 4

The following scalp deodorant composition, in lotion form is prepared as follows:

| | |
|---|---|
| 2,6-di tert. butyl p-cresol | 2 g |
| ethyl alcohol | 90 ml |
| perfume | 0.1 g |
| water sufficient for | 100 ml |

The pH of this lotion is 7.5.

EXAMPLE 5

A scalp deodorant composition, in lotion form, is prepared as follows:

| | |
|---|---|
| 2,6-di tert. butyl p-cresol | 1 g |
| ethyl alcohol | 90 ml |
| perfume | 0.1 g |
| water sufficient for | 100 ml |

The pH of this lotion is 7.5.

EXAMPLE 6

Another scalp deodorant composition according to the invention is prepared as follows:

| | |
|---|---|
| propyl gallate | 1 g |
| citric acid | 1 g |
| ethyl alcohol | 96 ml |
| perfume | 0.1 g |
| water sufficient for | 100 ml |

The pH of this lotion is 3.3.

EXAMPLE 7

The following scalp deodorant composition is prepared as follows:

| | |
|---|---|
| 2,6-di tert. butyl p-cresol | 1 g |
| citric acid | 1 g |
| ethyl alcohol | 96 ml |
| perfume | 0.1 g |
| water sufficient for | 100 ml |

The pH of this lotion is 2.4.

EXAMPLE 8

A scalp deodorant composition is prepared by mixing together:

| | |
|---|---|
| 2,6-di tert. butyl p-cresol | 1 g |
| sodium salt of ethylenediamine tetraacetic acid (EDTA) | 0.15 g |
| ethyl alcohol | 90 ml |
| perfume | 0.1 g |
| water sufficient for | 100 ml |

The pH of this lotion is 9.7.

EXAMPLE 9

A pressurized sprayable aerosol scalp deodorant composition is prepared as follows:

| | |
|---|---|
| 2,6-di tert. butyl p-cresol | 1 g |
| ethyl alcohol | 9 g |
| perfume | 0.2 g |
| Freon 11 | 30 g |
| Freon 12 | 60 g |

The pH is 6.9.

In the above Examples PVP/VA S.630 is a white powder having a ratio of PVP to VA of 60:40 and having a specific gravity (25°C) of 1.27 ± 0.01 determined on the molten copolymer. Its K-value ranges between 30–50 wherein the K-value is a function of means molecular weight and is derived from the formula:

$$\frac{\log_n \text{rel}}{C} = \frac{75K_o^2}{1 + 1.5K_oC} + K_o$$

wherein $K = 1000K_o$, $C$ = conc. in g/100 ml solu. and $n$ rel = viscosity of the solution compared to the solvent. Its Gardner-Haldt viscosity at 25°C in 25% ethanol is 50 centipoises. Freon 11 is trichloromonofluoromethane and Freon 12 is dichlorodifluoromethane.

The above compositions can also contain an organic acid or salt thereof such as citric acid, or the sodium salt of ethylenediamine tetraacetic acid, such as the tetrasodium salt thereof, in amounts ranging from about 0 to 1 weight percent of said composition. Additionally, conventional additives or adjuvants can also be incorporated into the compositions of this invention such as silicones, hair fixing agents, oxyethylenated derivatives of lanolin, surfactants, film-forming resins, quarternary ammonium compounds, vitamins, and panthenol derivatives.

What is claimed is:

1. A scalp deodorant composition for deodorizing the scalp and reducing excessive secretion of sebum from the scalp of a person having a scalp so characterized consisting essentially of a solution of, as the active agent, propyl gallate in amount of 0.1–3 percent by weight and ethylene diamine tetraacetic acid in amounts of 0–1 percent by weight, of said composition in a solvent selected from the group consisting of water, lower alkanol selected from the group consisting of ethyl alcohol and isopropyl alcohol and an aqueous solution of said lower alkanol containing 10 to 50 percent by weight of said lower alkanol, said composition having a pH ranging from about 2–10.

2. The composition of claim 1 wherein said active agent is present in amounts of about 0.5–1.5 percent by weight of said composition.

3. A process for deodorizing the scalp and reducing excessive secretion of sebum from the scalp of a person having a scalp so characterized comprising applying to the scalp in amounts effective to deodorize the same and to reduce said excessive sebum secretion the scalp deodorant composition of claim 1.

4. A scalp deodorant composition for deodorizing the scalp and reducing excessive secretion of sebum from the scalp of a person having a scalp so characterized consisting essentially of a solution of, as the active agent, 0.1–3 percent by weight of 2,6-di-tertiobutyl para cresol and 0.1–1 percent by weight of ethylene diamine tetraacetic acid in a solvent selected from the group consisting of water, lower alkanol selected from the group consisting of ethyl alcohol and isopropyl alcohol and an aqueous solution of said lower alkanol containing 10 to 50 percent by weight of said lower alkanol, said composition having a pH ranging from about 2–10.

5. The composition of claim 4 wherein said active agent is present in amounts of about 0.5–1.5 percent by weight of said composition.

6. A process for deodorizing the scalp and reducing excessive secretion of sebum from the scalp of a person having a scalp so characterized comprising applying to the scalp in amounts effective to deodorize the same and to reduce said excessive sebum secretion the scalp deodorant composition of claim 4.

7. A sprayable aerosol scalp deodorant composition for deodorizing the scalp and reducing excessive secretion of sebum from the scalp of a person having a scalp so characterized, said composition under pressure consisting essentially of a solution in a lower alkanol selected from the group consisting of ethyl alcohol and isopropyl alcohol of, as the active agent, propyl gallate, in amounts of 0.1–3 percent by weight of said composition and as the aerosol propellant a mixture of dichlorodifluoromethane and trichloromonofluoromethane present in amounts of about 50 to 90 percent by weight of said composition.

8. A sprayable aerosol scalp deodorant composition for deodorizing the scalp and reducing excessive secretion of sebum from the scalp of a person having a scalp so characterized, said composition under pressure consisting essentially of a solution in a lower alkanol selected from the group consisting of ethyl alcohol and isopropyl alcohol of, as the active agent, di-tertiobutyl para cresol in amounts of 0.1–3 percent by weight of said composition and as the aerosol propellant a mixture of dichlorodifluoromethane and trichloromonofluoromethane present in amounts of about 50 to 90 percent by weight of said composition.

* * * * *